US00PP08762P

United States Patent [19]

McRae

[11] Patent Number: Plant 8,762

[45] Date of Patent: May 31, 1994

[54] LILY PLANT LILIUM 'YELLOW FASHION'

[75] Inventor: Judith F. McRae, Boring, Oreg.

[73] Assignee: Mt. Hood Lilies, Inc., Sandy, Oreg.

[21] Appl. No.: 99,826

[22] Filed: Jul. 30, 1993

[51] Int. Cl.[5] ..... A01H 5/00

[52] U.S. Cl. ..... Plt./87.4

[58] Field of Search ..... Plt. 87.4

[56] Reference Cited

U.S. PATENT DOCUMENTS

PLT 6419 11/1988 Boon et al. ..... PLT/87.4

*Primary Examiner*—David T. Fox

[57] ABSTRACT

A new variety of hybrid lily plant bearings large upfacing to outfacing flowers of excellent form and long persistence, both on the plant and as cut-flowers. The flowers of the new hybrid are particularly characterized by their large size and substance, their "open bell" form, their yellow coloration, and their fragrance. This combination is completely new in the Longiflorum hybrid divisions of lilies suited to forcing and to mass commercial cultivation. The variety of highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 1988 in Boring, Ore. The breeding efforts had as their objective the production of colored, fragrant hybrids between *Lilium longiflorum* (the Easter lily) and Asiatic lilies, suited to forcing into flower out of season, heretofore unknown in the lily breeding art.

I achieved the desired objective by intercrossing a slightly fertile embryo-cultured seedling from (*Lithium longiflorum* 'Ace'×'Sterling Star') with 'Connecticut King.' The seed parent was the diploid form of the Dutch cultivar 'Longistar' (unpatented), which had limited commercial distribution in the Netherlands and the United States. This cultivar does not normally produce fertile seed; it can be used in breeding only if its embryos are artificially cultured. The pollen parent, 'Connecticut King,' although unpatented, has been extensively cultivated as a commercial cut-flower variety in the United States and the Netherlands. The embryo that produced 'Yellow Fashion' was artificially cultured as well.

The flowers of my new lily are characterized by an very large, fragrant, yellow upfacing to slightly outfacing flowers with an "open bell" form with slightly clawed tepals, quite narrow at the base and broadest just below the midpoint of the bud and flower, and with tepal tips flattening but recurving only slightly. This unique flower form is intermediate between the trumpet-form of *Lilium longiflorum* and the "flat-faced" Asiatic hybrid form with conspicuously recurved tepal tips. The new clone possesses unusually strong, stout stems. In addition, the clone possesses to a high degree desirable characteristics of hybrid vigor. The clone is a good grower and propagator, as observed at Boring, Ore.

My new variety of lily plant has been asexually reproduced by me and under my direction at Boring, Ore. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive yellow coloration and "open bell" flower and bud form (with tepals quite narrow at the apex and broadest just below the midpoint of the bud or tepal, with tepal tips opening wide and flattening but recurving only slightly at the tips).

DESCRIPTION OF THE NEW VARIETY

The following is a detailed description of my new variety of Longiflorum hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Embryo-cultured seedling.

*Seed parent.*—(*Lilium longiflorum* 'Ace'×'Sterling Star').

*Pollen parent.*—'Connecticut King'.

Commercial classification: Hybrid Lilium clone.

Horticultural classification: This clone best fits Division V. Longiflorum hybrid lily, according to the Horticultural Classification of Lilies, Royal Horticultural Society of London. This clone actually links Division V with Division I (Asiatic hybrids), however, indicating that the RHS Horticultural Classification will eventually have to be revised to accomodate such hybrids.

Form: Single stem, erect and stately.

Height: 75 to 150 cm from bulbs 14 to 20 cm in circumference, provided their light levels are adequate; low light levels may cause "stretching."

Growth: Vigorous and upright.

Foliage quantity: Abundant.

Size leaf: 10 to 15 cm long, 2 to 4 cm wide.

Shape of leaf: Lanceolate (pointed).

Texture: Leathery and glossy.

Color: Medium green, lighter on lower side.

Bulb size: Any size, ranging to 25 cm circumference commercially.

Bulb color: White, with flushes of pink or yellow after exposure to light.

The Bud

Form: Obtuse, ovoid, and long

Size: 10 to 14 cm long and 10 to 14 cm in circumference just prior to opening

Opening: Bud opens slowly, in response to morning light; this takes about one hour.

Color: RHS CC yellow 8 B to 13C, overlaid with RHS red 51 C along the midrib, and with green tips just prior to opening.

Peduncle: Averages 5 to 10 cm, but it may elongate if light levels are too low, if bulbs have been improperly stored prior to forcing, or if bulbs are very large, producing an unusually large inflorescence. Color is deep green to bronze.

The Flower

Blooming habit: Annually in midseason; flowers once and profusely.

Size: Flowers are very large-sized, averaging 15 to 20 cm in diameter, flattening at the tips on the second day to 15 to 18 cm in diameter. The tepals are broad: outer tepals are 3 to 4 cm wide, and the inner tepals are 5 to 8 cm wide.

Borne: In a single racemic inflorescence producing 8 to 20 flowers from a bulb 14 to 16 cm in circumference. Large bulbs produce an inflorescence with many secondary and even tertiary buds. In the larger inflorescences, the flowers are more outfacing and less upfacing.

Shape: Form a broad "open bell" shape by the second day after opening, quite narrow at the base and with the broadest part of the tepals just below their midpoint. The tepal tips flatten but recurve only slightly.

Tepalage: Typical of genus Lilium, with 6 imbricated tepals.

Tepal color: RHS CC yellow 13 B to 8 A/B. Heat and low light levels with produce a slightly less intense yellow color.

Tepal spotting: Variable but inconspicuous. 1 to 8 small magenta-black spots may appear at the base of each tepal, or they may be unspotted.

Tepal longevity: Tepals stay on stems about three weeks.

Pedicel length: Average 8 to 12 cm long.

Pedicel color: Dark green with light plum overlay; appears deep green to bronze to the eye.

Pedicel form: Sturdy and ascending. Large inflorescences may carry many secondary and tertiary buds, in which case many of the pedicels become more horizontal.

Color changes: Flowers become slightly lighter as the flowers age. Low light levels and extreme heat may also cause them to become lighter.

Appearance: Flower is shiny.

Nectaries: present on both inner and outer tepals, substantially typical of the Asiatic Hybrid class, lightly pubescent with hairs or callouses of RHS yellow 13 D, slightly lighter than the flower color.

Disease resistance: The flower and plant are resistant to disease; in particular, they are resistant to Fusarium bulb rot and Botrytis blight.

Fragrance: Fragrance similar to that of *Lilium longiflorum*, but lighter.

Lasting quality: The flower is long lasting, both on the plant and as a cut-flower.

The Reproductive Organs

Stamens: Arrangement typical of genus Lilium. Six stamens with soft yellow to slightly green-yellow filaments 7 to 9 cm long.

Pollen anthers (dehisced): RHS CC yellow orange 23 A to greyed orange 163 A.

Pistil: One in number, very soft yellow-green, 7 to 9 cm long.

Stigma: Soft yellow green to white, large in size.

Characteristics of ovary: Characteristics of genus Lilium.

The Fruit

Fertility: The fruit bears a few fertile seed, but most embryos require embryo culturing.

Shape: Ovoid.

Color at maturity: Soft brown, overlaid with soft plum.

My new variety of *Lilium longiflorum*/Asiatic hybrid lily most nearly resembles 'Longistar' in flower form, but it has a deeper "bell" form, broader tepals, and rounder tips. It is yellow in color rather than cream-white, and it has more fragrant flowers. It also resembles its embryo-cultured sibling 'Yellow Ace' (unregistered name), but 'Yellow Ace' has completely outfacing flowers with distinctly pointed tepals, with 20 or more deep magenta spots at the base of each tepal.

I claim:

1. A new and distinctive variety of *Lilium longiflorum*/Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower/pot plant produced from pre-cooled bulbs forced under glass out of season; and in particular by its unique fragrant yellow "open bell" flowers, a combination unique among hybrid lilies suited to forcing and to mass commercial cultivation.

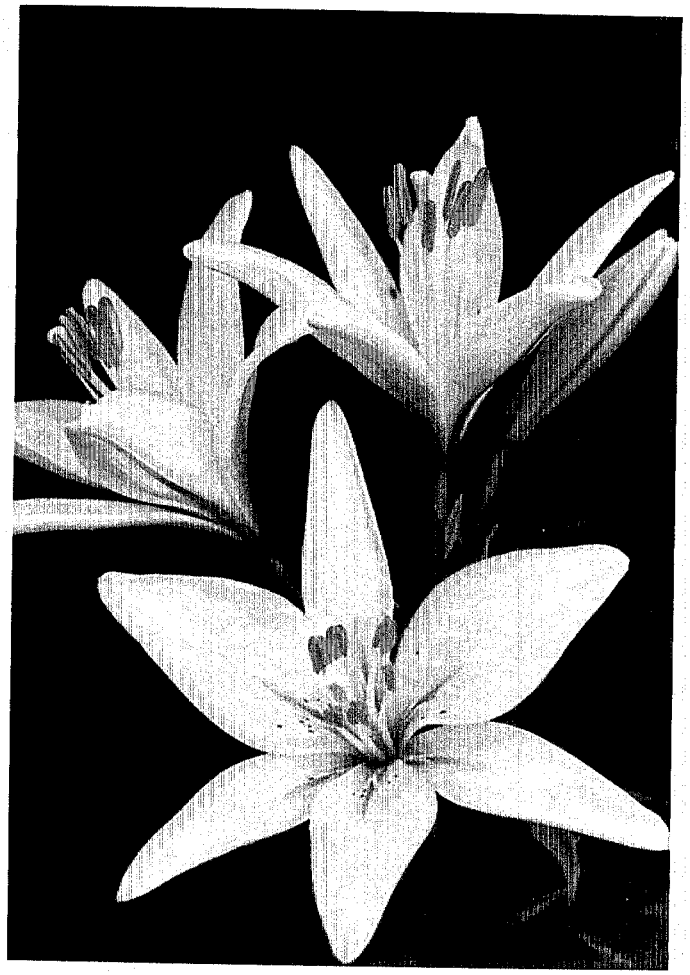

* * * * *